(12) United States Patent
Lee

(10) Patent No.: US 8,777,435 B2
(45) Date of Patent: Jul. 15, 2014

(54) AROMA LAMP

(76) Inventor: Huan-Ping Lee, Toufen Township, Miaoli County (TW)

( * ) Notice: Subject to any disclaimer, the term of this patent is extended or adjusted under 35 U.S.C. 154(b) by 195 days.

(21) Appl. No.: 13/587,930

(22) Filed: Aug. 17, 2012

(65) Prior Publication Data

US 2014/0049941 A1     Feb. 20, 2014

(51) Int. Cl.
| | |
|---|---|
| F21V 33/00 | (2006.01) |
| A61L 9/14 | (2006.01) |
| A61L 9/12 | (2006.01) |

(52) U.S. Cl.
CPC . *F21V 33/00* (2013.01); *A61L 9/14* (2013.01); *A61L 9/122* (2013.01); *A61L 2209/12* (2013.01)
USPC ............................................. 362/92; 362/101

(58) Field of Classification Search
None
See application file for complete search history.

(56) References Cited

U.S. PATENT DOCUMENTS

| | | | |
|---|---|---|---|
| 8,529,078 B2* | 9/2013 | Lee | 362/96 |
| 2004/0022675 A1* | 2/2004 | An | 422/29 |
| 2007/0159422 A1* | 7/2007 | Blandino et al. | 345/82 |

* cited by examiner

*Primary Examiner* — Britt D Hanley
(74) *Attorney, Agent, or Firm* — Leong C. Lei

(57) ABSTRACT

The aroma lamp contains a base a base within which a circuit board is housed. On the circuit board, there is a fan, an atomization element, and a number of light generation elements. The base also has a short tube and a cap housing the fan and connecting the short tube. The aroma lamp further contains a container having a top opening. The container is joined to the base and stores the liquid to be atomized. The container has an axial tube connecting the top opening and the short tube of the base and a valve element for releasing the liquid to the base. The aroma lamp also contains a cover having a top opening aligned with the top opening of the container. The cover is joined to the base and houses the container. The atomized vapor is released through the top openings of the container and the cover.

13 Claims, 10 Drawing Sheets

AROMA LAMP

(a) TECHNICAL FIELD OF THE INVENTION

The present invention generally relates to aroma lamps, and especially relates to an aroma lamp integrating a fan to speed up atomization.

(b) DESCRIPTION OF THE PRIOR ART

A conventional lamp usually contains a lamp base and a light generation element. Even though some lamp has a lamp shade to add to the lamp's visual appealing, but the effect is limited as the opaque lamp shade conceals the various colors produced by the light generation element. On the other hand, there are so called aroma lamps. For these lamps, the aroma is usually dissipated by some monotonous means, and is not coordinated with the lamp's illumination.

Therefore, the present inventor, after long research and development, has provide a novel aroma lamp to obviate the foregoing shortcomings of the prior art.

SUMMARY OF THE INVENTION

A major objective of the present invention is to atomize liquid by supersonic vibration and to use a fan to speed up atomization and aroma spreading.

Another objective of the present invention is to integrate light generation elements so that more varieties are added to the aroma lamp.

The aroma lamp contains a base a base within which a circuit board is housed. On the circuit board, there is a fan, an atomization element, and a number of light generation elements. The aroma lamp further contains a container having a top opening. The container is joined to the base and stores the liquid to be atomized. The container has an axial tube connecting the top opening and a short tube of the base. The aroma lamp also contains a cover having a top opening aligned with the top opening of the container. The cover is joined to the base and houses the container. The atomized vapor is released through the top openings of the container and the cover.

Preferably, the fan is housed in a cap of the base.

Preferably, the container further contains a valve element controlling the flow of the container's liquid to an indentation on top of the base.

Preferably, the cap is connected to the short tube so that air is blown from the fan through the short tube into the axial tube.

The aroma lamp of the present invention not only can provide ordinary illumination, but also can present various visual effects and atmosphere by integrating different light generation elements.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
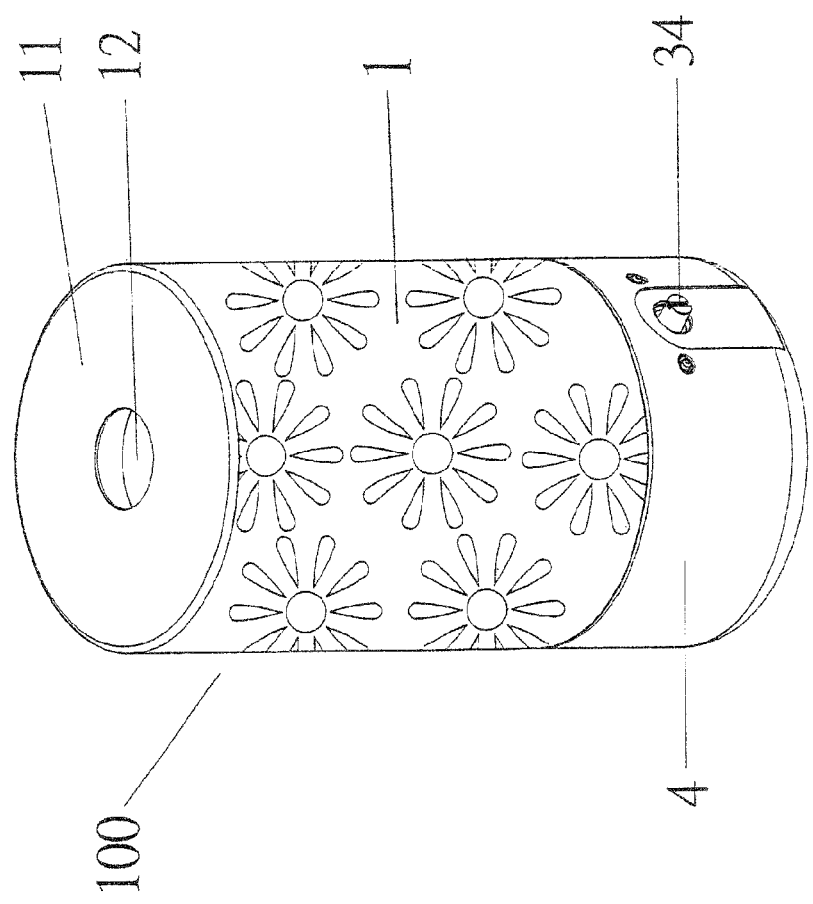
FIG. 1 is a perspective diagram showing an aroma lamp according to an embodiment of the present invention.
Figure 2:
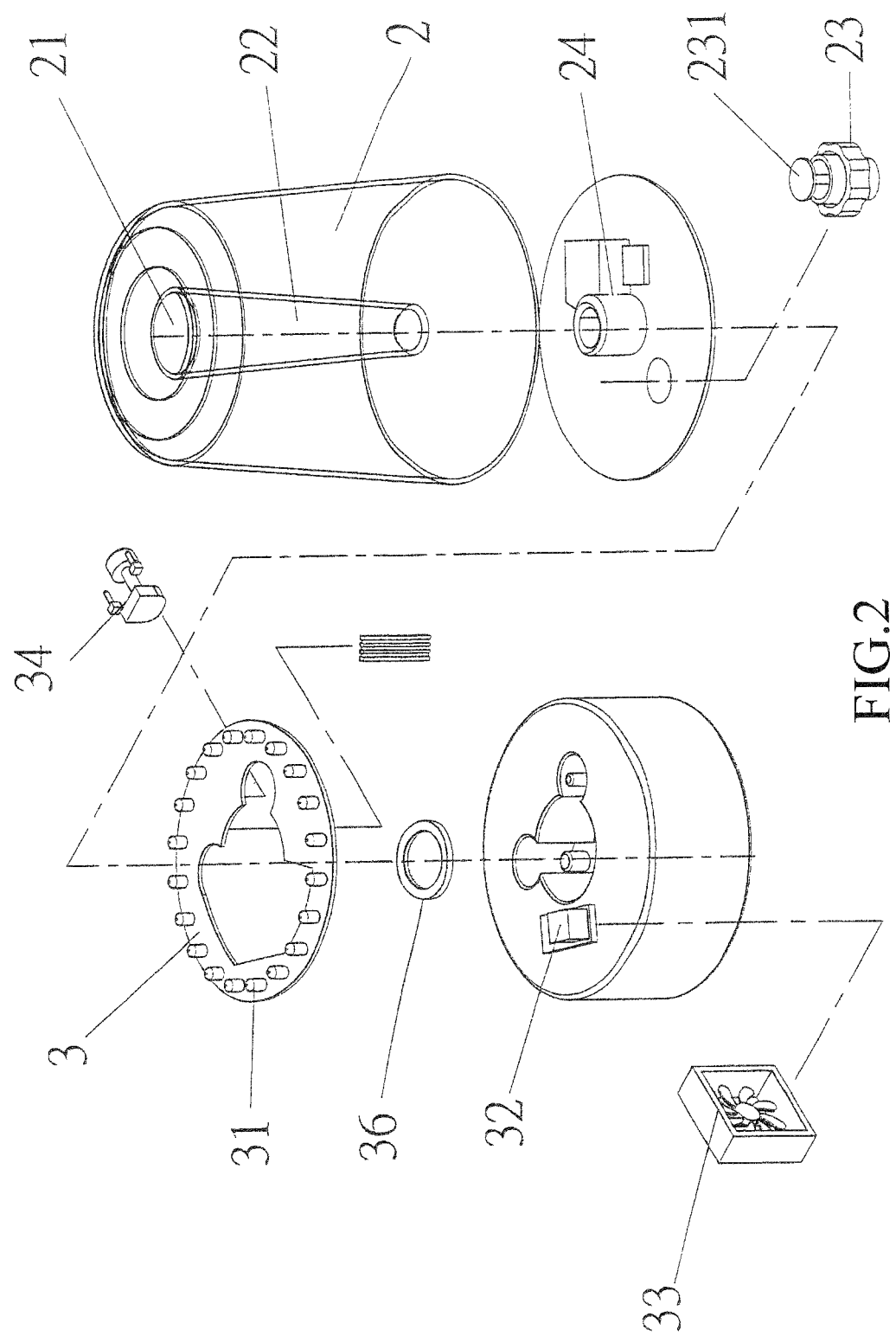
FIG. 2 is a perspective break-down diagram showing the various components of the aroma lamp of FIG. 1.
Figure 3:
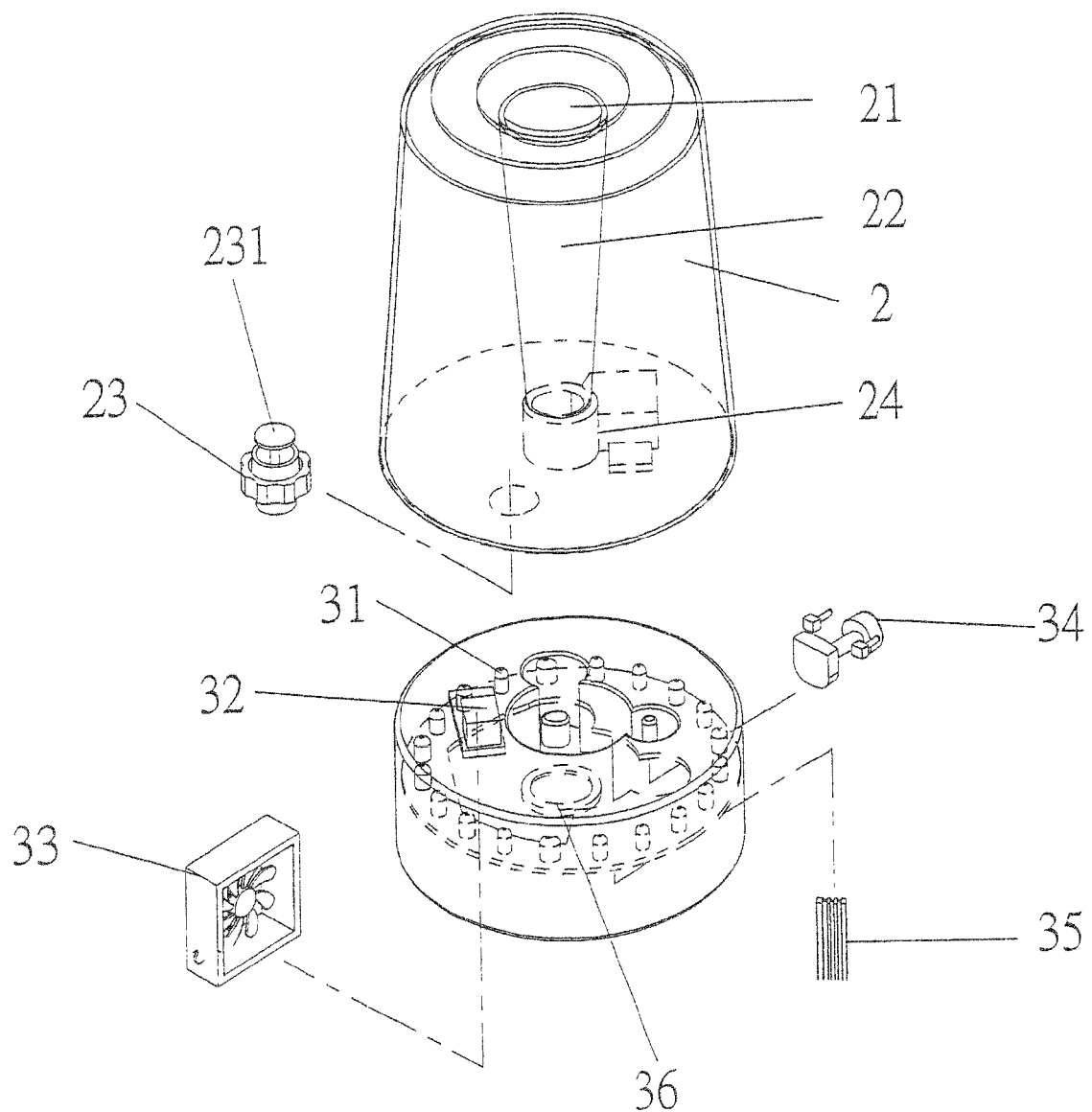
FIG. 3 is a perspective diagram showing the aroma lamp of FIG. 2 that is partially assembled.

As shown in FIGS. 1 to 3, where the appearance and internals of an aroma lamp 100 according to an embodiment of the present invention are depicted, the aroma lamp 100 contains a base 4 within which a circuit board 3 is housed. On the circuit board 3, there is a fan 33, an atomization element 36, and a number of light generation elements 31. On a bottom side of the circuit board 3, the is also a switch 34 for turning on/off the fan 33 and the light generation elements 31 and a heat dissipation piece 35 for dissipating extraneous heat of the circuit board 3. The aroma lamp 100 further contains a container 2 having a top opening 21. The container 2 is joined to the base 4 and stores the liquid to be atomized. The container 2 has an axial tube 22 connecting the top opening 21, and a valve element 23 for controlling the flow of the liquid into a Mickey-shaped indentation on top of the base 4. The aroma lamp 100 also contains a cover 1 having a top opening 12 on a top side 11 aligned with the top opening 21 of the container 2 after the cover 1 is joined to the base 4 and houses the container 2. The top opening 12 is for releasing the atomized vapor. Each light generation element 31 can be a light emitting diode (LED), a cold cathode fluorescent lamp (CCFL), or an organic LED (OLED). The base 4 can be made of wood, ceramics, glass, plastics, or fiber optics. The container 2 and the cover 1 can be made of ceramics, glass, plastics, and fiber optics.

Figure 4:
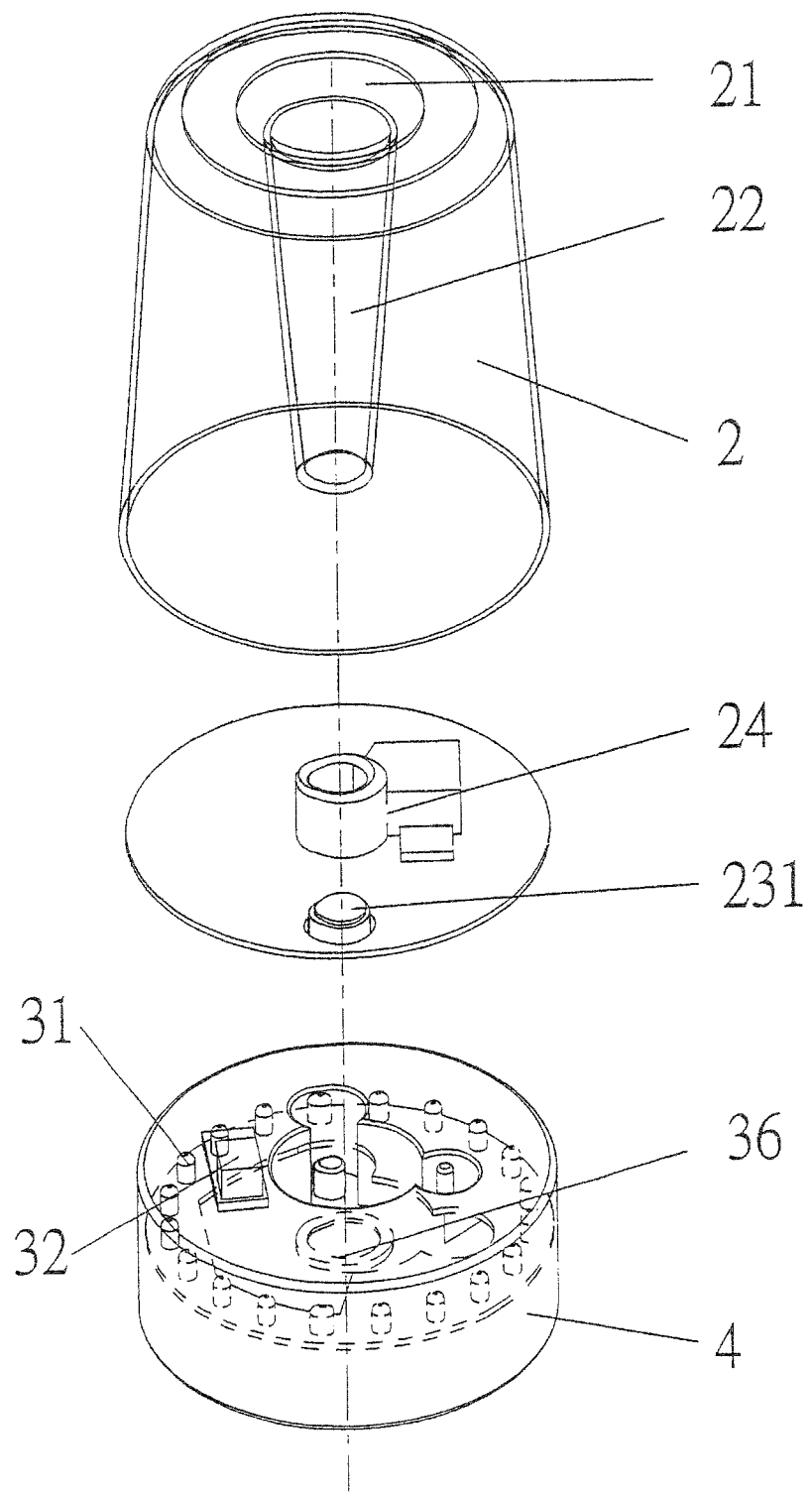
FIG. 4 is another perspective diagram showing the aroma lamp of FIG. 2 that is partially assembled.
Figure 5:
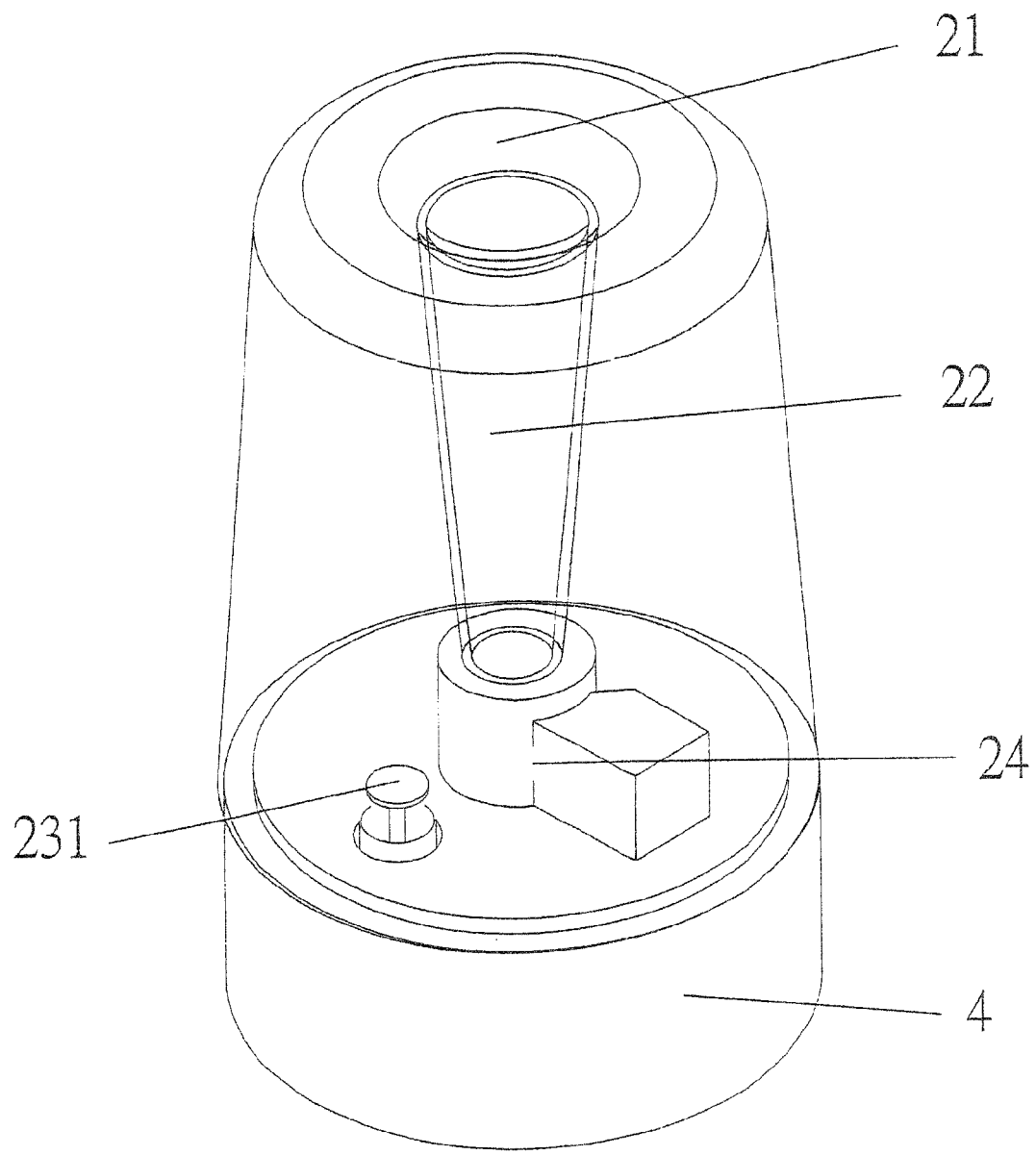
FIG. 5 is a perspective diagram showing the aroma lamp of FIG. 1 without the cover.

As shown in FIGS. 4 and 5, where the aroma lamp 100 is partially assembled, the liquid to be atomized can be added to the container 2 by removing a bottom piece of the container 2 or through a hole left by removing the valve element 23. A watertight pad 231 is configured on top of the valve element 23. When the container 2 is not placed on the base 4, the watertight pad 231 maintains a close state, preventing the liquid from leaking. When the container 2 is placed on the base 4, a protrusion inside the indentation presses a spring inside the valve element 23 and turns the watertight pad 231 into an open state, thereby allowing liquid to flow through the valve element 23 into the indentation. The liquid in the indentation is then atomized through supersonic vibration by the atomization element 36.

Figure 6:
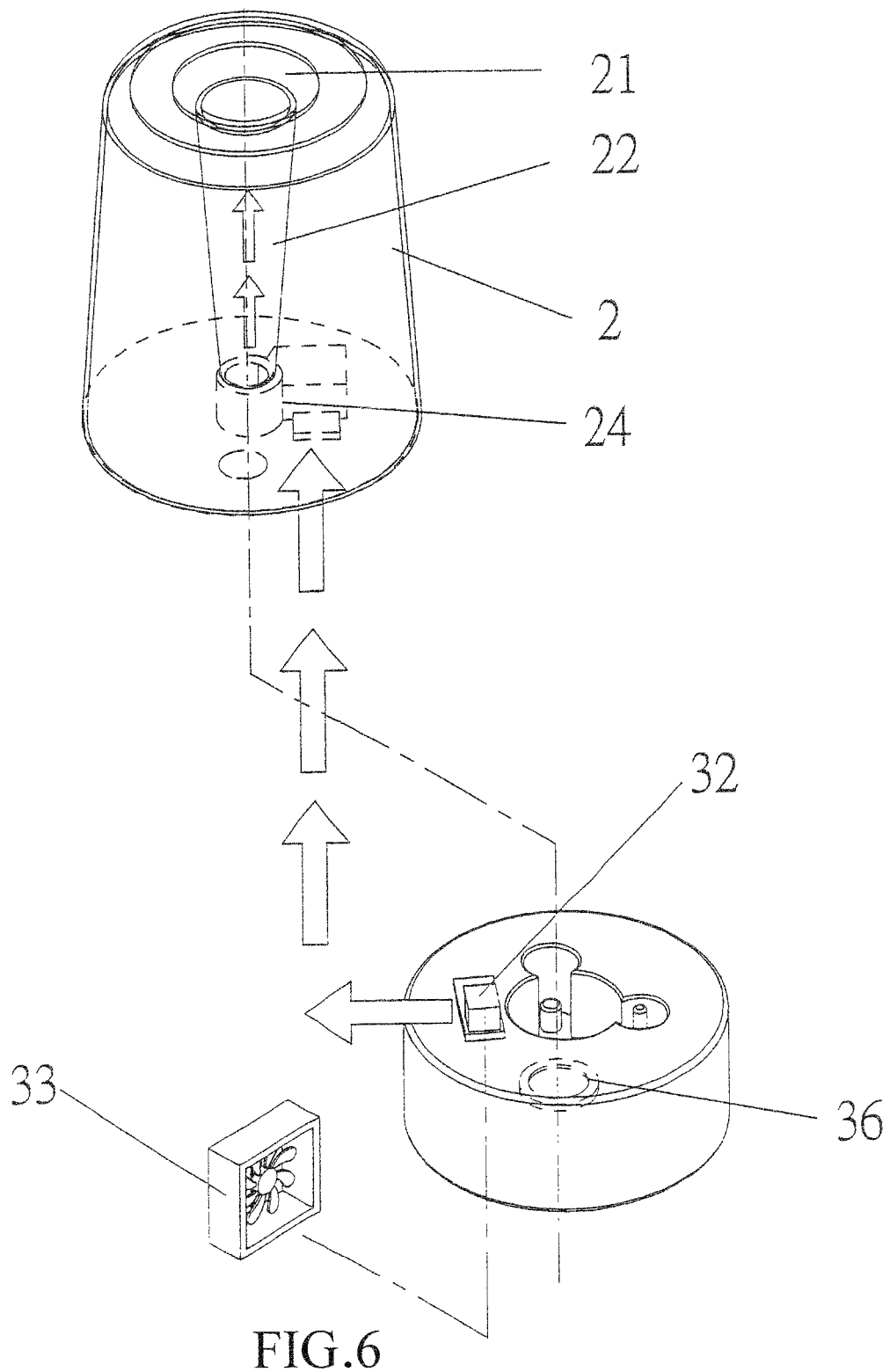
FIG. 6 is a perspective diagram showing the path of atomized vapor for the aroma lamp of FIG. 1.
Figure 7:
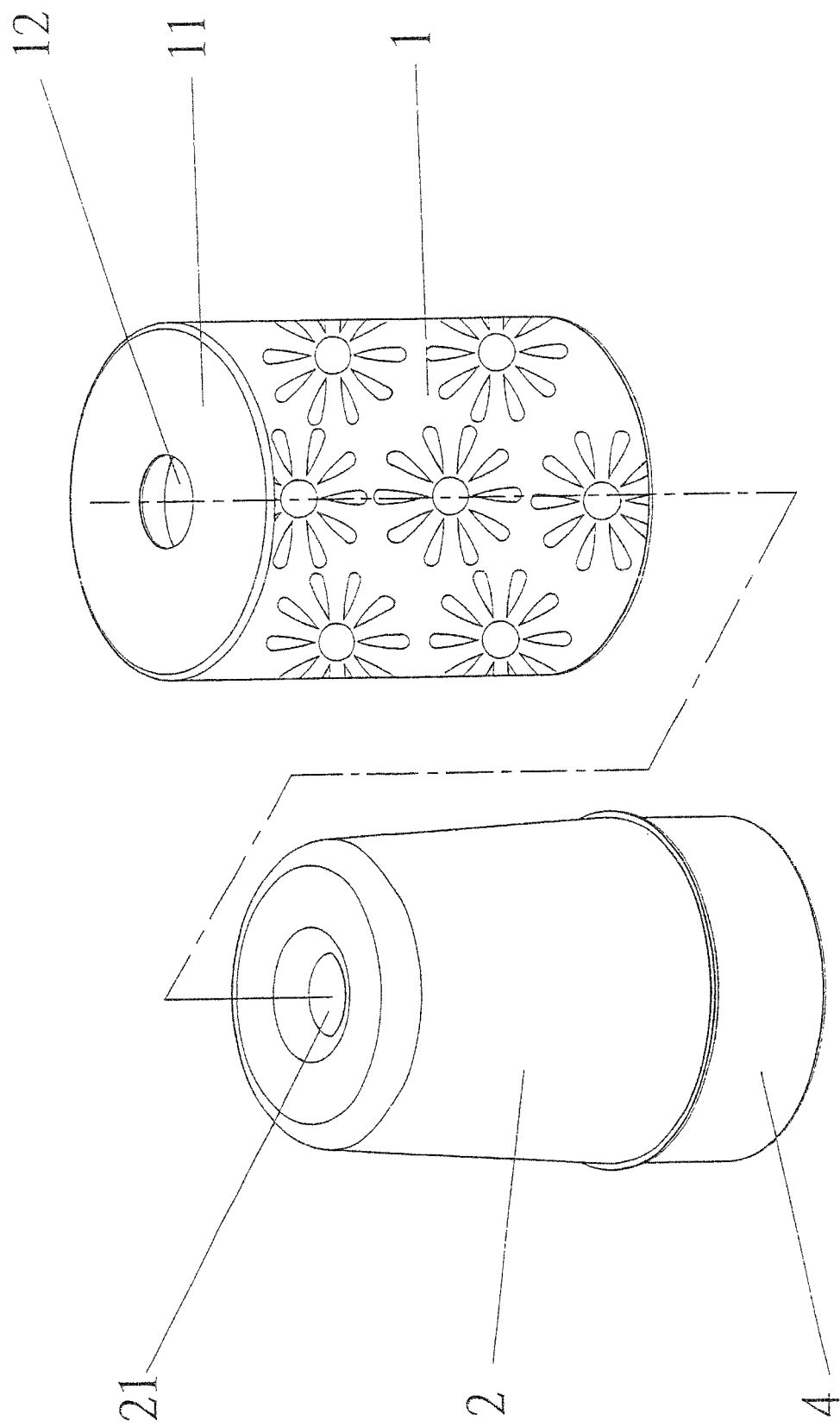
FIG. 7 is a perspective diagram showing the installation of the cover for the aroma lamp of FIG. 1.
Figure 8:
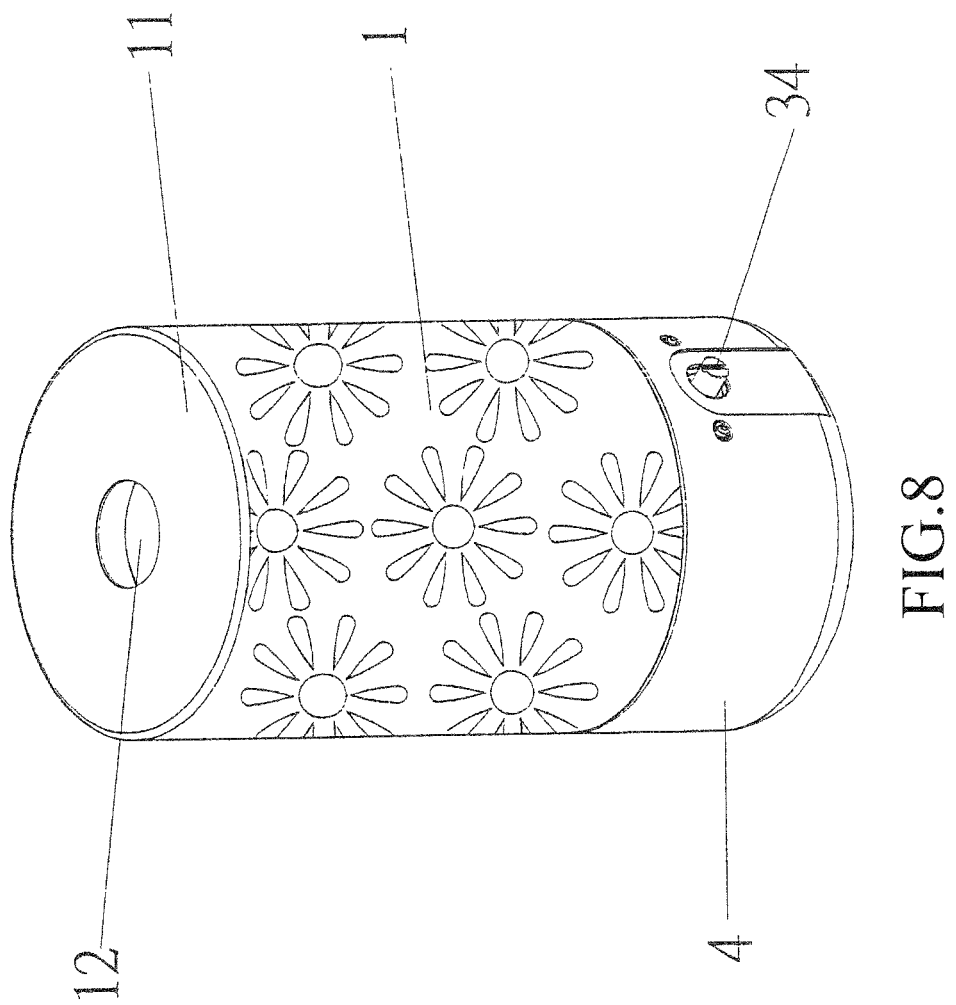
FIG. 8 is a perspective diagram showing the aroma lamp of FIG. 1 after its assembly.

As shown in FIGS. 6 to 8, where the path of the released atomized vapor and the completed assembly of the aroma lamp 100 are depicted, the base 4 has a cap 32 connected to a short tube 24, both integrally formed with the base 4. The fan 33 is housed inside the cap 32 and the short tube 24 is connected with the axial tube 22 of the container 2. The atomized vapor is blown by the fan 33 into the axial tube 22 through the short tube 24. The atomized vapor is then released into the atmosphere through the top opening 21 of the container 2 and the top opening 12 of the cover 1. The liquid stored in the container 2 can be mixed with alcohol or bactericide for sterilization, or with water to increase the humidity of the atmosphere and to prevent respiratory illness, or with ethereal oil for spreading refreshing fragrance.

Figure 9:
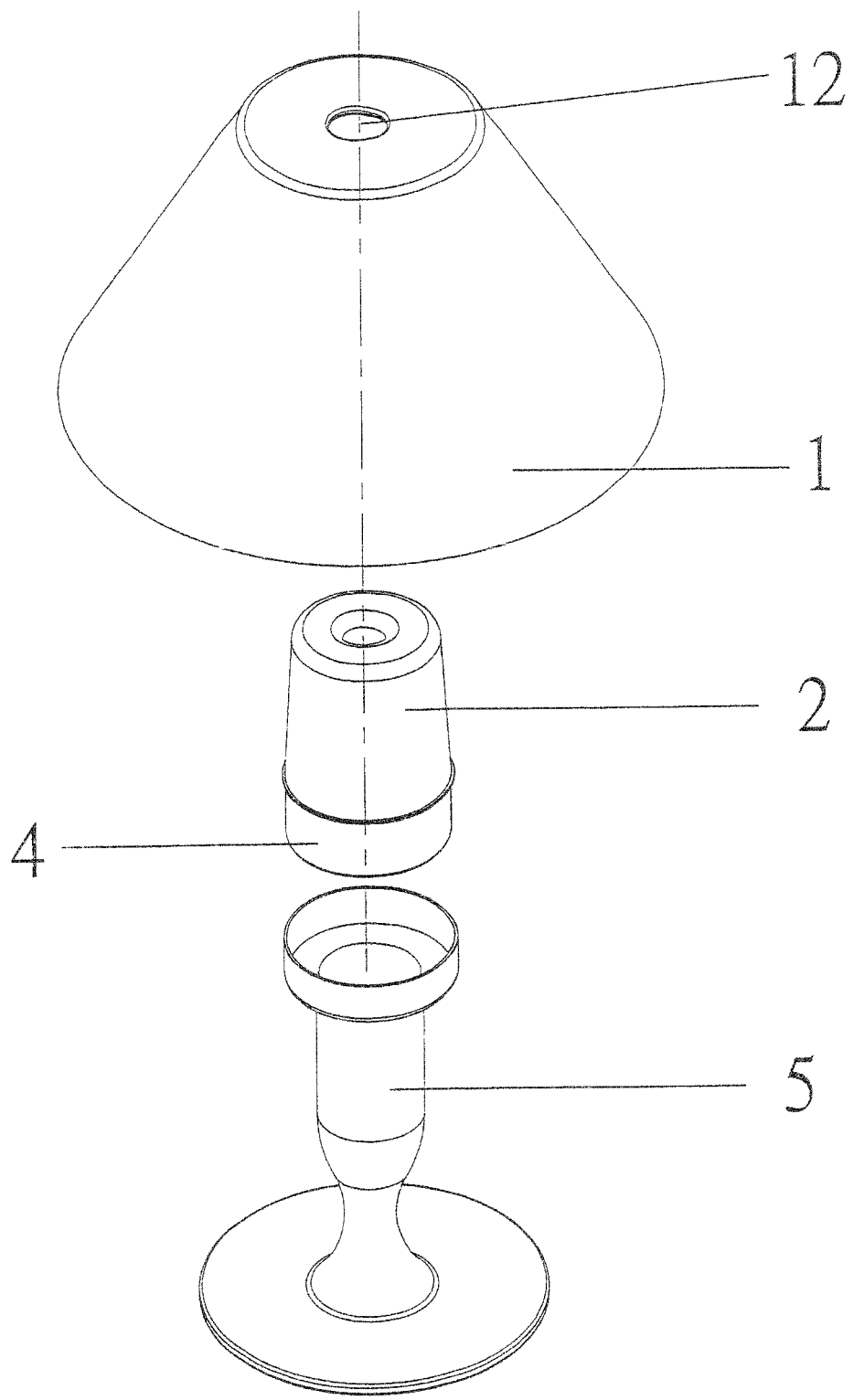
FIG. 9 is a perspective diagram showing an alternative embodiment of the present invention.
Figure 10:
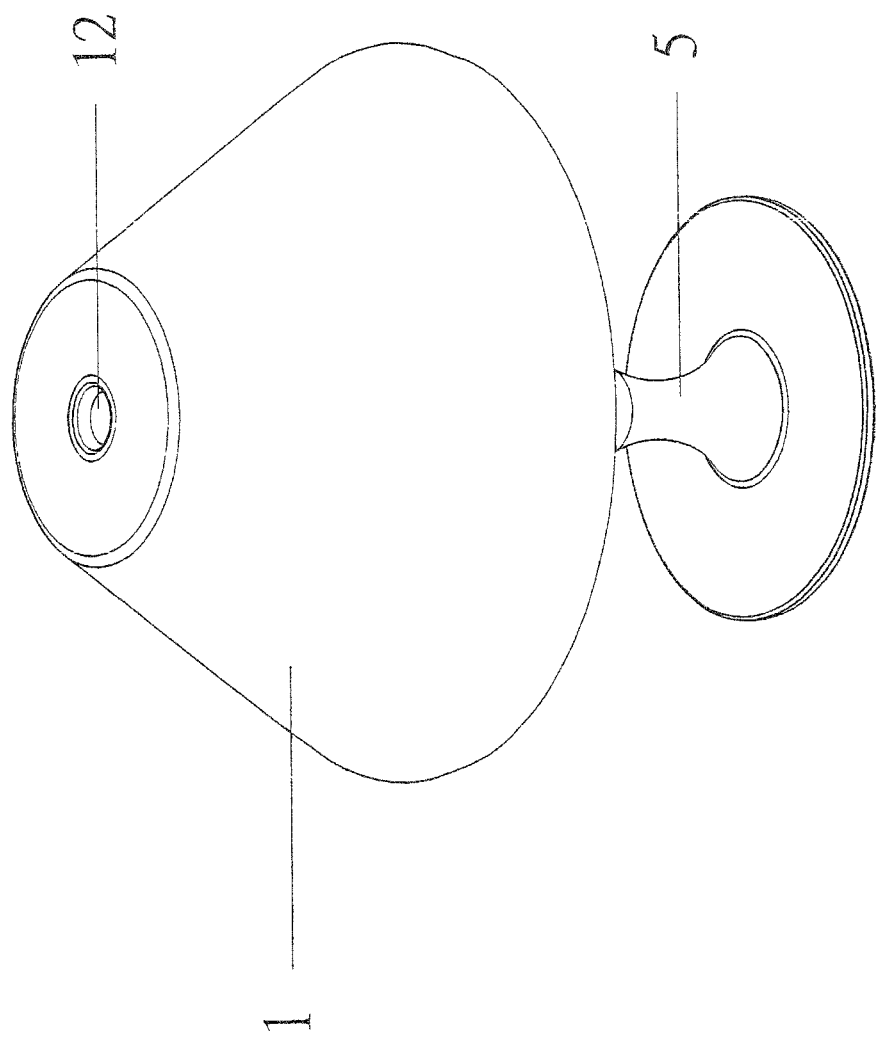
FIG. 10 is a perspective diagram showing aroma lamp of FIG. 9 after its assembly.

As shown in FIGS. 9 and 10, where an alternative embodiment of the aroma lamp 100 is depicted, the cover 1 is not limited to a specific shape. The cover 1 can be shaped like a lamp shade so that the aroma lamp 100 functions like a table lamp. In addition, the aroma lamp 100 can also be placed on various pedestals 5 so that the aroma lamp 100 can have broader application.

Please note that the aroma lamp 100 can be turned on/off or controlled manually (e.g., using the switch 34), or through remote control. Please also note that the aroma lamp 100 can be powered by the mains by plugging into a wall socket or by a battery inside the base 4.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. An aroma lamp, comprising:
   a base having a circuit board inside, the circuit board having a fan, an atomization element, and a plurality of light generation elements;
   a container joined to the base, the container storing a liquid to be atomized, and having a top opening and an axial tube connecting the top opening; and
   a cover joined to the base and housing the container, the cover having a top opening aligned with the top opening of the container;
   wherein the liquid is atomized by the atomization element and the atomized vapor is blown by the fan and released to the atmosphere through the axial tube and the top openings of the container and the cover.

2. The aroma lamp according to claim 1, wherein the base further comprises a cap housing the fan.

3. The aroma lamp according to claim 1, wherein the container further comprises a valve element for controlling the flow of the liquid in the container to an indentation on top of the base.

4. The aroma lamp according to claim 2, wherein the base further comprises a short tube connecting the axial tube of the container and the cap so that air is blown from the fan through the short tube into the axial tube.

5. The aroma lamp according to claim 1, wherein the top opening of the cover is configured on a top side of the cover.

6. The aroma lamp according to claim 1, wherein each light generation element is one of light emitting diode (LED), cold cathode fluorescent lamp (CCFL), and organic LED (OLED).

7. The aroma lamp according to claim 1, wherein the atomization element is a supersonic vibration device.

8. The aroma lamp according to claim 1, wherein the liquid to be atomized is a combination of at least one of alcohol, water, and ethereal oil.

9. The aroma lamp according to claim 1, wherein the base is made of one of wood, ceramics, glass, plastics, and fiber optics.

10. The aroma lamp according to claim 1, wherein the container is made of one of ceramics, glass, plastics, and fiber optics.

11. The aroma lamp according to claim 1, wherein the cover is made of one of wood, ceramics, glass, plastics, and fiber optics.

12. The aroma lamp according to claim 1, wherein the aroma lamp is powered by the mains or by a battery.

13. The aroma lamp according to claim 1, wherein the aroma lamp is operated manually or through remote control.

* * * * *